United States Patent
Maitland

(10) Patent No.: US 7,393,524 B2
(45) Date of Patent: Jul. 1, 2008

(54) BACULOVIRUS VECTORS COMPRISING A CAPSID POLYPEPTIDE FUSED TO A GNRH POLYPEPTIDE

(75) Inventor: Norman Maitland, York (GB)

(73) Assignee: Procure Therapeutics Limited, York (GB)

( * ) Notice: Subject to any disclaimer, the term of this patent is extended or adjusted under 35 U.S.C. 154(b) by 173 days.

(21) Appl. No.: 10/486,698

(22) PCT Filed: Aug. 15, 2002

(86) PCT No.: PCT/GB02/03791

§ 371 (c)(1),
(2), (4) Date: Sep. 9, 2004

(87) PCT Pub. No.: WO03/016540

PCT Pub. Date: Feb. 27, 2003

(65) Prior Publication Data

US 2005/0009184 A1  Jan. 13, 2005

(30) Foreign Application Priority Data

Aug. 15, 2001 (GB) ................................. 0119852.2

(51) Int. Cl.
*A01N 63/00* (2006.01)
*A01N 65/00* (2006.01)
*A01N 43/04* (2006.01)
*A61K 48/00* (2006.01)
*A61K 31/70* (2006.01)

(52) U.S. Cl. ......................................... 424/93.1; 514/44
(58) Field of Classification Search ........................ None
See application file for complete search history.

(56) References Cited

U.S. PATENT DOCUMENTS 5,885,808 A * 3/1999 Spooner et al. ............. 435/456
5,962,424 A * 10/1999 Hallahan et al. ............... 514/44
6,183,993 B1 * 2/2001 Boyce et al. ................ 435/69.7
6,238,914 B1 * 5/2001 Boyce ....................... 435/320.1

FOREIGN PATENT DOCUMENTS

| CA | 2 300 361 A1 | 2/1999 |
| DE | 19735593 | 2/1999 |
| WO | WO 94/08022 | 4/1994 |
| WO | WO 00/58470 | 10/2000 |
| WO | WO 00/77233 | 12/2000 |
| WO | WO-0077233 A2 * | 12/2000 |

OTHER PUBLICATIONS

Zhau, et al. (1996) Proc. Natl. Acad. Sci., USA, 93: 15152-57.*
Anderson, et al. (2000) Radiation Research, 154: 473-76.*
Daftarian, et al. (2004) Cancer Research, 64(15): 5407-14.*
Fuxe, et al. (2000) Cell Growth and Differentiation, 11: 373-84.*
Haeffner, et al. (1999) European Journal of Immunology, 29: 334-44.*
Takai, et al. (2001) Journal of Biochemistry, 1: 5-12.*
Lavoie, et al. (2000) Journal of Cell Biology 150(5): 1037-55.*
Kumagai, et al. (1996) Cancer Research, 56: 354-58.*
Shewchuk, et al. (2000) Structure, 8: 1105-13.*
Lachyankar, et al. (2000) Journal of Neuroscience, 20(4): 1404-13.*
Lu, et al. (2001) Journal of Biological Chemistry, 276(16): 13442-51.*
Collis, et al. (2001) Nucleic Acids Research, 29(7): 1534-38.*
Ojala, et al. (2001) Biochemical and Biophysical Research Communications, 284: 777-84.*
Gu, et al. (1999) Cancer Research, 59: 2608-14.*

* cited by examiner

*Primary Examiner*—Joseph Woitach
*Assistant Examiner*—Robert Kelly
(74) *Attorney, Agent, or Firm*—Crowell & Moring LLP

(57) ABSTRACT

The invention relates to a genetically engineered baculovirus wherein said virus is engineered to target therapeutic agents to cells, typically cancer cells, for example prostate cancer cells.

6 Claims, 5 Drawing Sheets

```
                          SEQUENCE LISTING

<160> NUMBER OF SEQ ID NOS: 4

<210> SEQ ID NO 1
<211> LENGTH: 44
<212> TYPE: DNA
<213> ORGANISM: Homo sapiens

<400> SEQUENCE: 1
ctgcagcaac attggagcta cggcttgcgc ccgggcgcgg tacc              44

<210> SEQ ID NO 2
<211> LENGTH: 14
<212> TYPE: PRT
<213> ORGANISM: Homo sapiens

<400> SEQUENCE: 2

Leu Gln Gln His Trp Ser Tyr Gly Leu Arg Pro Gly Ala Val
1               5                   10
```

-continued

```
<210> SEQ ID NO 3
<211> LENGTH: 53
<212> TYPE: DNA
<213> ORGANISM: Homo sapiens

<400> SEQUENCE: 3
ctgcaggaat tgtacgaaaa caaaccgcgc cgcccgtaca ttttggcggt acc          53

<210> SEQ ID NO 4
<211> LENGTH: 17
<212> TYPE: PRT
<213> ORGANISM: Homo sapiens

<400> SEQUENCE: 4

Leu Gln Gln Leu Tyr Glu Asn Lys Pro Arg Arg Pro Tyr Ile Leu Ala
1               5                   10                  15

Val
```

BACULOVIRUS VECTORS COMPRISING A CAPSID POLYPEPTIDE FUSED TO A GNRH POLYPEPTIDE

The invention relates to a baculovirus wherein the baculovirus genome comprises a nucleic acid molecule encoding a therapeutic agent and a nucleic acid molecule which encodes a polypeptide wherein said polypeptide functions to target the baculovirus to at least one cell type; methods of treatment using said baculovirus and pharmaceutical compositions comprising said baculovirus.

Gene therapy involves the transfer, and optionally the stable insertion, of new genetic information into cells for the therapeutic treatment of disease. The main issues with respect to gene therapy relate to the efficient targeting of nucleic acid to cells and the establishment of high level transgene expression in selected tissues. A number of methodologies have been developed which purport to facilitate either or both of these requirements. For example, U.S. Pat. No. 6,043,339 discloses the use of signal peptides which when fused to a nucleic acid can facilitate the translocation of the linked nucleic acid across cell membranes. U.S. Pat. No. 6,083,714 discloses a combined nucleic acid and targeting means which uses the polycation poly-lysine coupled to an integrin receptor thereby targeting cells expressing the integrin. EP1013770 discloses the use of nuclear localisation signals (NLS) coupled to oligonucleotides. The conjugate may be covalently linked to vector DNA and the complex used to transfect cells. The NLS sequence serves to facilitate the passage of the vector DNA across the nuclear membrane thereby targeting gene delivery to the nucleus.

A range of viral based vectors have been used to successfully transfect mammalian cell lines. These include adenovirus, adenovirus-associated virus, papovaviruses and vacciniavirus. These viral based vectors have considerable disadvantages. Adenovirus vectors are well established in gene therapy trials, although recent difficulties in the USA may restrict their use. (Wickham T J, Gene therapy, 7: 110, 2000). The major problems appear to be non-selective cytotoxicity (particularly in the liver) and pre-existing immune responses against the virus. The cytolytic T cell response induced against adenovirus capsid-derived peptides has been shown to mediate the destruction of vector transduced cells and has been associated with localised tissue damage and inflammation. (Gilgenkrantz, H. et al. (1995) Hum Gene Ther 6, 1265-1274; Yang, Y. and Wilson, J. M. (1995) J Immunol 155, 2564-2570). The possibility of recombination with endogenous infecting adenovirus, particularly at high input dose, is also a potential safety concern.

Limitations to the amount of extra genetic material inserted into recombinant viruses are imposed by the defined size of the adenovirus capsid. Adenoviruses will recombine with pre-existing material; a potential drawback where endogenous adenovirus is wide spread in the human population. Similarly it has been demonstrated that adenovirus vectors have the ability to aid the replication of related endogenous human viruses.

Safety concerns are also associated with the clinical use of Herpes Simplex Virus. Lytic replication of the virus in the human brain has been linked to encephalitis. (Latchman, D. S. (1994). Mol Biotechnol 2, 179-195).

Although retroviral vectors are widely used in clinical trials, a number of disadvantages are associated with these vectors. Integration into cells is random, a major safety concern. Use of these vectors is limited, as they require dividing cells for infectivity.

An alternative vector, which has been shown to infect mammalian cells, is the baculovirus. Baculovirus is a rod form virus and therefore limitations to the amount of genetic material inserted into recombinant baculovirus is not as limiting as those imposed by adenovirus capsid.

The baculovirus will not express its own genes from insect-specific promoters in human cells. This is an attractive feature since the baculovirus will not provoke an immune response as a consequence of viral gene expression of virally encoded genes. However, insertion of a marker or therapeutic gene under control of a mammalian promoter allows high level expression of the transgene. Unlike the adenovirus vector, baculovirus will not recombine with pre-existing material. Infection with baculovirus will not facilitate the replication of endogenous human viruses, as has been demonstrated with adenovirus vectors. In contrast to many of the other therapeutic viruses, baculoviruses can be grown in a serum free culture media in large quantities. This method of production can be readily scaled up to industrial level and removes the potential hazards of serum contamination of the therapeutic agent with viral and prion agents. Most importantly, unlike all other human viral vectors, there is no pre-existing immune response against baculovirus in humans.

The construction of recombinant baculovirus is well documented. EP0340359, which is incorporated by reference, discloses a method of obtaining a recombinant baculovirus incorporating a foreign gene through use of a transfer vector. The novel transfer vector incorporates a restriction site a short distance downstream of the N-terminus of the polyhedrin gene body, into which a foreign gene may be cloned. The natural ATG start codon for the polyhedrin gene is not provided, such that the N-terminal polyhedrin coding sequence prior to the restriction site is retained but not capable of translation. A recombinant baculovirus incorporating a foreign gene is derived from the transfer vector by co-transfecting insect cells susceptible to baculovirus infection with wild type baculovirus and the transfer vector.

Similarly U.S. Pat. No. 6,126,944, which is incorporated by reference, relates to the construction of baculovirus transfer vectors for efficient expression of foreign genes, and more particularly expression of glycoprotein gG1 and gG2 of the Herpes Simplex virus. The foreign gene to be expressed is juxtaposed with the baculovirus polyhedrin gene at the translation initiation site, without the addition of further nucleotides to the initiation site.

U.S. Pat. No. 5,750,383, which is incorporated by reference, discloses a baculovirus cloning system. The system is a marker rescue system using an essential gene. The selected essential gene is inactivated. Cloning into the baculovirus containing the null mutation is then achieved by using the virus to infect wild type host cells that are co-infected with a plasmid containing a functional copy of the gene linked to a foreign gene under the control of a regulatable promoter. The baculovirus null mutation is "rescued" by the rescue gene linked to a foreign gene. The function of the essential gene is restored and the foreign gene is expressed. An example of an essential gene is gp64 efp (envelope fusion protein), that encodes a protein essential for viral infectivity and propagation.

Although disclosing methods by which baculovirus may be manipulated the prior art is not related to the use of baculovirus as a viral vector for targeted gene therapy.

We have developed a recombinant baculovirus which includes targeting sequences incorporated into the baculovirus genome which facilitate the delivery of the baculovirus and thereby the therapeutic agent to a specific cell type.

An example of a candidate gene for targeting is the baculovirus gp64, an extensively processed type 1 integral membrane glycoprotein. The role of gp64 in baculovirus infectivity has been demonstrated by the neutralization of infectivity with antibodies specific to gp64. It has also been shown that gp64 is both necessary and sufficient for low pH activated membrane fusion activity. Although conclusive data has been lacking, indirect data on the role of gp64 in the infection cycle strongly suggests that the protein is essential for infectivity of the baculovirus.

The baculovirus gp64 envelope protein has been found to be sufficiently mutable to allow rapid insertion of new and more specific attachment sequences, without perturbing its function as a carrier of genetic information. The gp64 envelope protein has a long loop, which has previously been used for antigen presentation and is ideal for insertions. When modified gp64 is expressed together with wild type gp64 in a mosaic membrane viral infectivity is not grossly affected.

According to a first aspect of the invention there is provided a baculovirus wherein the baculovirus genome has been modified to include a nucleic acid molecule which encodes a therapeutic agent and a nucleic acid molecule which encodes a polypeptide which functions to target said baculovirus to at least one cell type.

In a preferred embodiment said baculovirus genome is adapted for eukaryotic gene expression of said nucleic acid molecules.

Typically said adaptation includes, by example and not by way of limitation, the provision of transcription control sequences (promoter sequences) which mediate cell/tissue specific expression. These promoter sequences may be cell/tissue specific, inducible or constitutive.

Promoter is an art recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences and is therefore position independent). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors (please see Eukaryotic Transcription Factors, by David S Latchman, Academic Press Ltd, San Diego) is responsive to a number of environmental cues.

Promoter elements also include so called TATA box and RNA polymerase initiation selection (RIS) sequences which function to select a site of transcription initiation. These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell or prokaryotic host.

Adaptations which facilitate the expression of baculovirus encoded genes include the provision of transcription termination/polyadenylation sequences. This also includes the provision of internal ribosome entry sites (IRES) which function to maximise expression of baculovirus encoded genes arranged in bicistronic or multi-cistronic expression cassettes.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

In a preferred embodiment of the invention said eukaryotic expression is through the provision of cancer cell specific promoter elements. Preferably, said promoters are active in prostate cancer cells.

More preferably the promoter elements are selected from the group as represented in Table 1.

In a preferred embodiment of the invention said therapeutic agent is a polypeptide.

Preferably said polypeptide is a tumour suppressor polypeptide selected from the following group represented in Table 2.

In a further preferred embodiment of the invention said polypeptide is an antigenic polypeptide.

Preferably a tumour rejection antigen precursor selected from the following families represented in Table 3.

In a further preferred embodiment said polypeptide is a prostate tumour rejection antigen.

In a further preferred embodiment of the invention said polypeptide is a cytotoxic polypeptide. For example pseudomonas exotoxin, ricin toxin, diptheria toxin (Genbank acc.#: A04646).

In a yet further preferred embodiment of the invention said polypeptide is a polypeptide which induces cell-cycle arrest.

Preferably said cell-cycle arrest polypeptide is selected from the group represented in Table 4.

In a further preferred embodiment of the invention said therapeutic polypeptide is a pharmaceutically active polypeptide. Preferably said polypeptide is a cytokine.

Preferably said cytokine is selected from the group represented in Table 5.

In a yet further preferred embodiment of the invention said polypeptide is an antibody, or active binding fragment thereof, for example a Fab fragment.

Antibody fragments smaller than Fab fragments which bind cellular targets are also within the scope of the invention. For example, single chain Fv molecules (scFv).

These are engineered antibody fragments composed of a variable region of the heavy chain and a variable region of the light chain which are coupled via a linker sequence, see Adams and Schier (1999) Journal of Immunological Methods 249-260.

In a yet still further preferred embodiment of the invention said polypeptide is a polypeptide which induces apoptosis.

Preferably said apoptosis inducing polypeptide is represented in Table 6.

In a yet still further preferred embodiment of the invention said polypeptide is a pro-drug activating polypeptide.

Preferably said prodrug activating polypeptide is represented in Table 7.

In a still further preferred embodiment of the invention said polypeptide has anti-angiogenic activity. For example angiostatin, Tie2 (Genbank acc. no: AF451865), endostatin (Genbank acc.no: NM130445).

In a further preferred embodiment of the invention said therapeutic agent is an antisense nucleic acid molecule.

As used herein, the term "antisense nucleic acid molecule" or "antisense" describes a nucleic acid which hybridizes under physiological conditions to DNA comprising a particular gene or to an mRNA transcript of that gene and thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense nucleic acid and its degree of complementarity with its target will depend upon the specific target selected, including the sequence of the target and the particular bases, which comprise that sequence.

It is preferred that the antisense nucleic acid be constructed and arranged so as to bind selectively with the target under physiological conditions, i.e., to hybridize substantially more to the target sequence than to any other sequence in the target cell under physiological conditions.

Although nucleic acids may be chosen which are antisense to any region of the gene or mRNA transcripts, in preferred embodiments the antisense nucleic acid correspond to N-terminal or 5' upstream sites such as translation initiation, transcription initiation or promoter sites. In addition, 3'-untranslated regions may be targeted. The 3'-untranslated regions are known to contain cis acting sequences which act as binding sites for proteins involved in stabilising mRNA molecules. These cis acting sites often form hair-loop structures which function to bind said stabilising proteins. A well known example of this form of stability regulation is shown by histone mRNA's, the abundance of which is controlled, at least partially, post-transcriptionally.

The present invention, thus, contemplates a baculovirus genome which has been modified by incorporation of an antisense nucleic acid to a specific target sequence, for example a target sequence encoding a cell-cycle regulatory gene, (eg p21 (Genbank acc.#: NM_078467, c-myc (Genbank acc.#: D10493 and D90467), cyclin dependent kinase inhibitors, p16 (Genbank acc.#:NM058196), p15 (Genbank acc.#: BC002010), p18 (mouse ssequence Genbank acc.#: BC027026), or p19 (Genbank acc.#: NM_079421) and apoptosis inhibitors such as caveolin.

In a further preferred embodiment of the invention said therapeutic agent is a double stranded RNA molecule. In this embodiment the baculovirus genome would include a nucleic acid molecule under the control of a first promoter positioned upstream (ie 5' of the nucleic acid molecule) and a second promoter positioned downstream (ie 3' of the nucleic acid molecule). The orientation of the promoters being such that both sense and antisense nucleic acid molecules are produced.

A technique to specifically ablate gene function is through the introduction of double stranded RNA, also referred to as inhibitory RNA (RNAi), into a cell which results in the destruction of mRNA complementary to the sequence included in the RNAi molecule. The RNAi molecule comprises two complementary strands of RNA (a sense strand and an antisense strand) annealed to each other to form a double stranded RNA molecule. The RNAi molecule is typically derived from exonic or coding sequence of the gene which is to be ablated. Alternatively said RNAi molecule is derived from intronic sequences or the 5' and/or 3' non-coding sequences which flank coding/exon sequences of genes. Recent studies suggest that RNAi molecules ranging from 100-1000 bp derived from coding sequence are effective inhibitors of gene expression. Surprisingly, only a few molecules of RNAi are required to block gene expression which implies the mechanism is catalytic. The site of action appears to be nuclear as little if any RNAi is detectable in the cytoplasm of cells indicating that RNAi exerts its effect during mRNA synthesis or processing.

The exact mechanism of RNAi action is unknown although there are theories to explain this phenomenon. For example, all organisms have evolved protective mechanisms to limit the effects of exogenous gene expression. For example, a virus often causes deleterious effects on the organism it infects. Viral gene expression and/or replication therefore needs to be repressed. In addition, the rapid development of genetic transformation and the provision of transgenic plants and animals has led to the realisation that transgenes are also recognised as foreign nucleic acid and subjected to phenomena variously called quelling (Singer and Selker, Curr Top Microbiol Immunol. 1995;197:165-77), gene silencing (Matzkeand Matzke, Novartis Found Symp. 1998;214:168-80; discussion 181-6. Review) and co-suppression (Stam et. al., Plant J. 2000;21(1):27-42.

In a still further preferred embodiment said therapeutic agent is a ribozyme.

A ribozyme is a catalytic RNA which is well known in the art. A ribozyme comprises a catalytic core having flanking sequences adjacent to the sequence which hybridises to the substrate RNA. The simplest catalytic core is an RNA motif known as a hammerhead. Since the discovery of catalytic RNA there has been a desire to design ribozymes which have a targetted gene function such that disease gene mRNA's can be selectively ablated.

In yet a further preferred embodiment of the invention the baculovirus genome includes a nucleic acid molecule which encodes a polypeptide which binds the baculovirus to the cell surface of at least one cell type.

In a preferred embodiment of the invention said nucleic acid encodes a polypeptide selected from the following group: GnRH (Genbank acc.no: L03380), fibroblast growth factors; insulin and insulin-like growth factors; neurotensin platelet derived growth factor (Genbank acc.no: NM_002609 & NM_006206); somatostatin (Genbank acc.no:BC032625).

In a preferred embodiment of the invention the nucleic acid encoding said polypeptide is inserted into the baculovirus genome at a site which fuses said polypeptide to a baculovirus capsid polypeptide. Preferably the capsid polypeptide is gp64.

Advantageously the fusion of the targeting polypeptide to a capsid polypeptide will result in its presentation at the baculovirus particle surface thereby presenting the baculovirus to said cell type and thereby facilitating cell targeting.

According to a further aspect of the invention there is provided a pharmaceutical composition comprising the baculovirus according to any previous aspect or embodiment of the invention. Preferably said composition is for use in the manufacture of a medicament for the treatment of cancer, ideally prostate cancer.

According to a yet further aspect of the invention there is provided a method of treatment comprising the administration of a therapeutically effective amount of the baculovirus according to the invention.

In a preferred method of the invention said treatment is cancer, preferably prostate cancer.

An embodiment of this invention will now be provided by example only and with reference to the following materials, methods, vectors and figures.

MATERIALS AND METHODS

Targeting baculoviruses are generated in two stages (i) by generation of a transfer vector in a bacterial plasmid, which is multiplied in bacteria, and whose DNA sequence in determined to verify the insertion of the recombinant DNA sequence; and (ii) recombination of the transfer vector, via homologous non essential region on either side of the gp64 recombinant, into a multiply cut Bv genome by cotransfection into recipient insect cells (sf9 or sf21).

An example of the experimental procedure is as follows.

Figure 3:
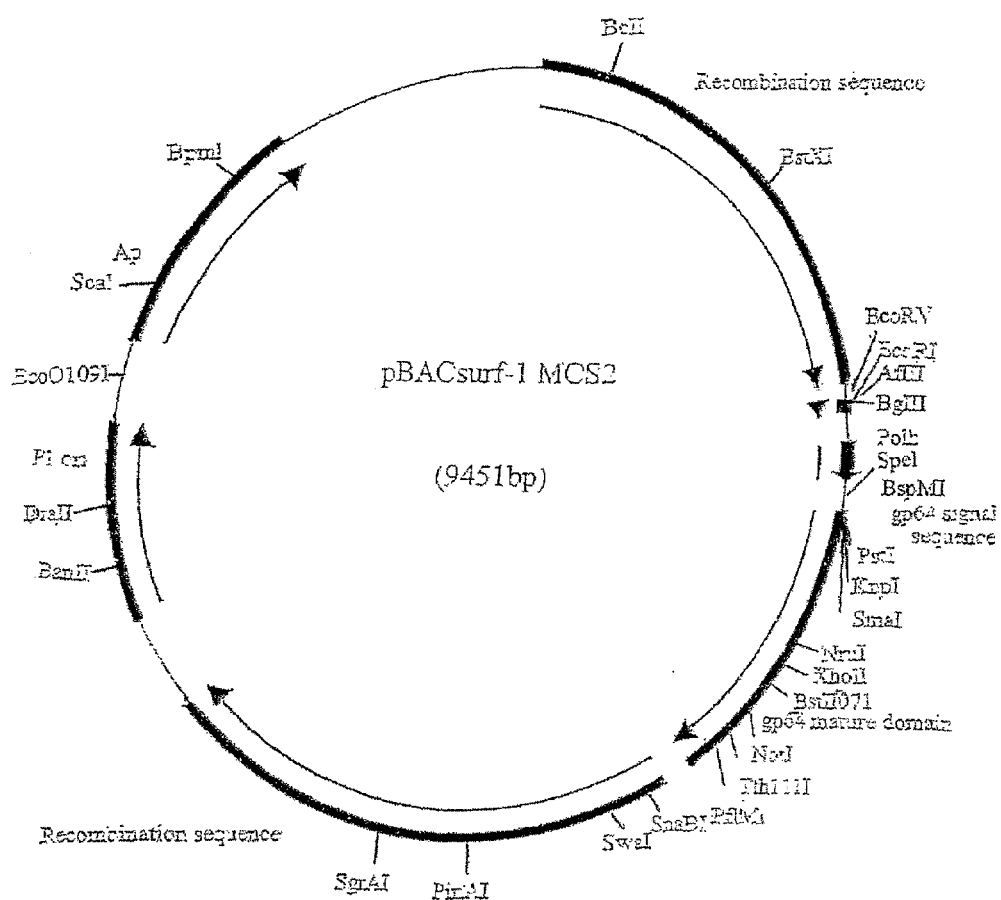
FIG. 3 is baculovirus vector pBAsurf-1 MCS2.
Figure 4:
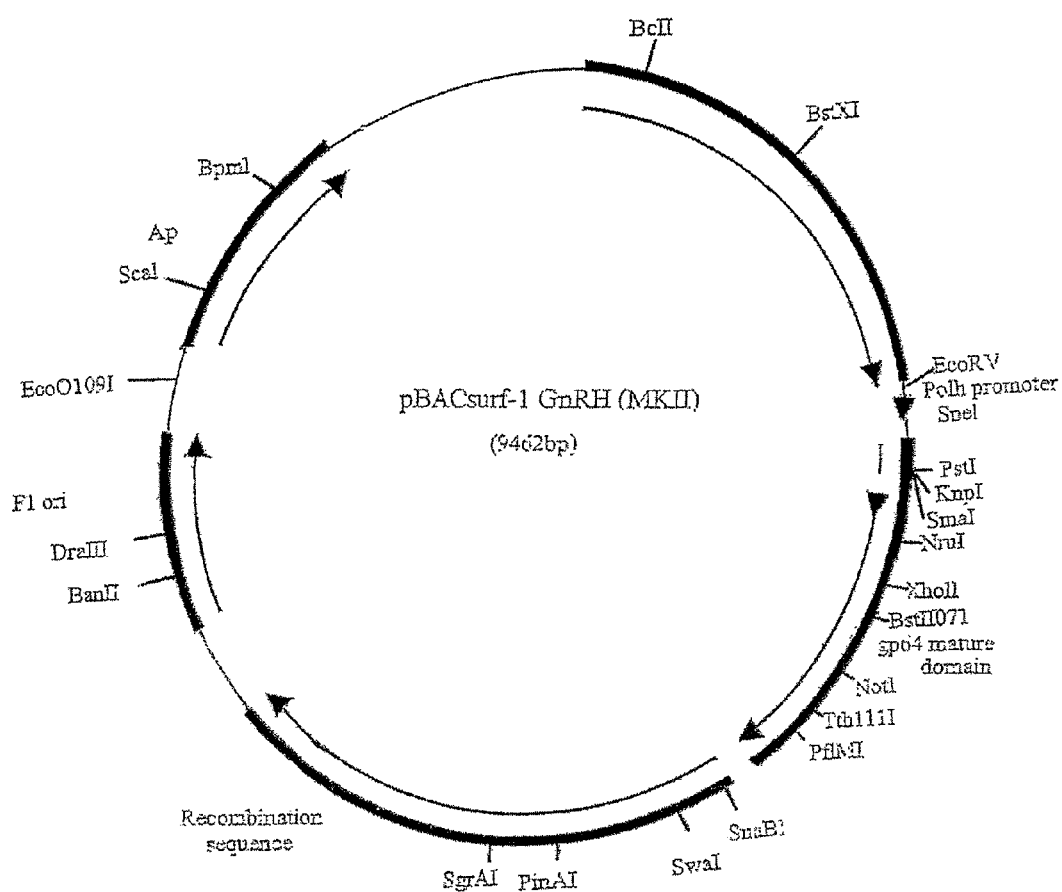
FIG. 4 is baculovirus vector pBAsurf-1 GnRH(MKII)
Figure 5:
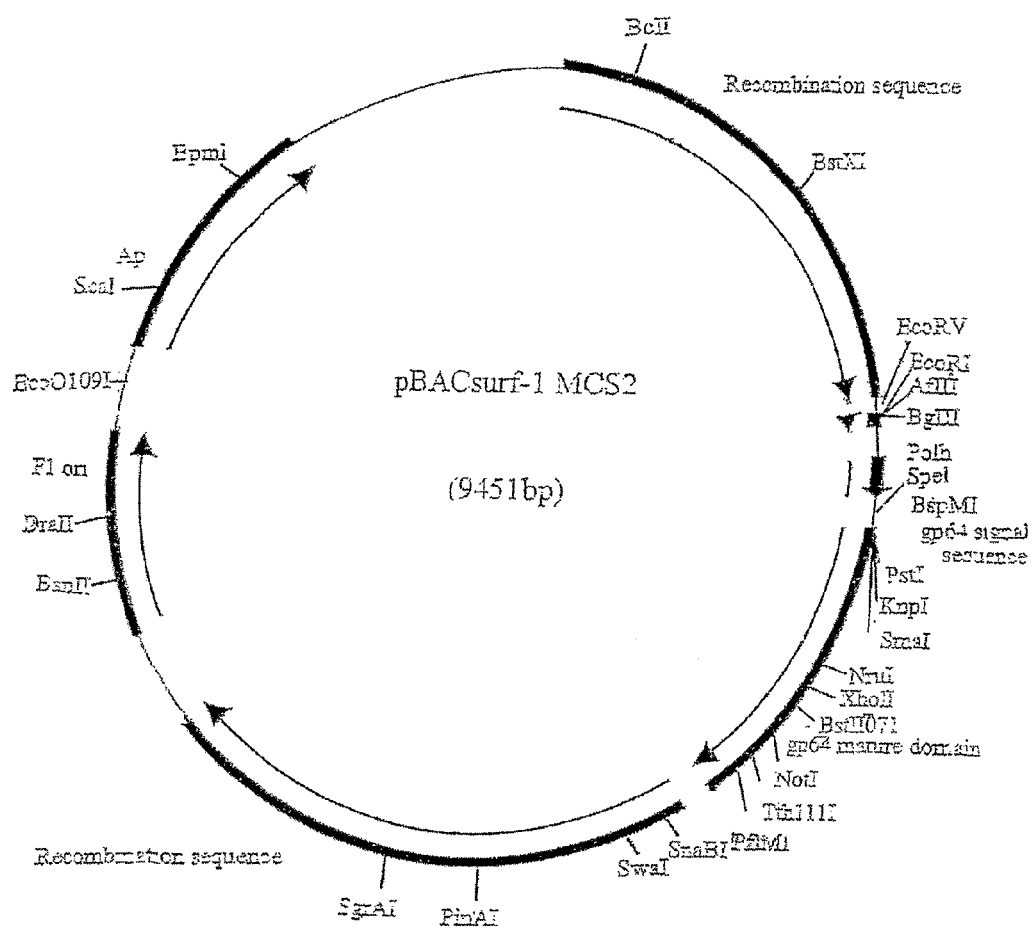
FIG. 5 is baculovirus vector pBacMam2 EGFP.

The DNA sequence encoding the minimal peptide required for receptor binding for the GnRH and neurotensin receptors was determined and a DNA oligonucleotides for both strands were chemically synthesised, including PstI and KpnI restriction endonuclease sites to facilitate insertion into the pBACsurf vector (FIG. 3). The synthesised oligonucleotides were then ligated into the pBACsurf vector via these restriction endonuclease sites The sequences of the peptides and a map of the vector are shown below, see FIG. 4 and FIG. 5:

```
GnRH peptide coding sequence          (SEQ ID NO: 1)
CTGCAGCAACATTGGAGCTACGGCTTGCGCCCGGGCGCGGTACC GnRH amino acid sequence              (SEQ ID NO: 2)
LeuGlnGlnHisTrpSerTyrGlyLeuArgProGlyAlaVal Neurotensin peptide coding sequence(SEQ ID NO: 3)
CTGCAGGAATTGTACGAAAACAAACCGCGCCGCCCGTACATTTTGGCGGT
ACC Neurotensin peptide                   (SEQ ID NO: 4)
LeuGlnGluLeuTyrGluAsnLysProArgArgProTyrIleLeuAla
Val
```

Full DNA sequence data for the constructs should be available for the final constructs, particularly the segment of the gp64 fusion protein.

The sequenced plasmid is then recombined into the Bacvector-1000 triple cut baculovirus DNA (Novagen) by cotransfection into sf21 cells. The resulting baculoviruses are only viable if recombination has occurred, and are diploid for the gp64 gene, as insertion does not occur in the native gp64 locus. This is essential to preserve high infectivity of the baculovirus, and has been observed in other systems eg HIV, where env protein modification can be carried out.

Figure 1:
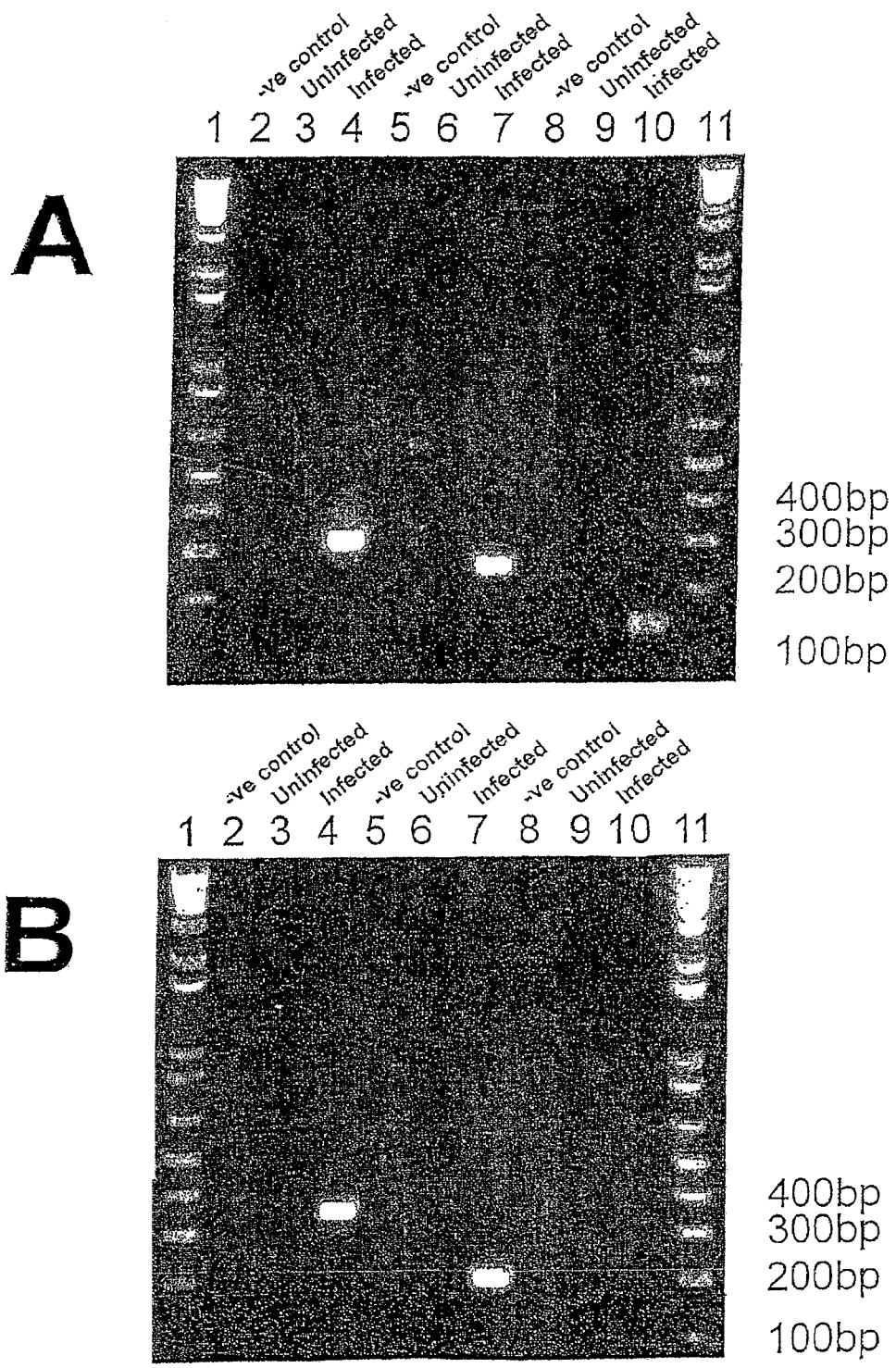
FIG. 1 illustrates baculoviral expression of AcMNPV in insect cells, Sf9.
Figure 2:
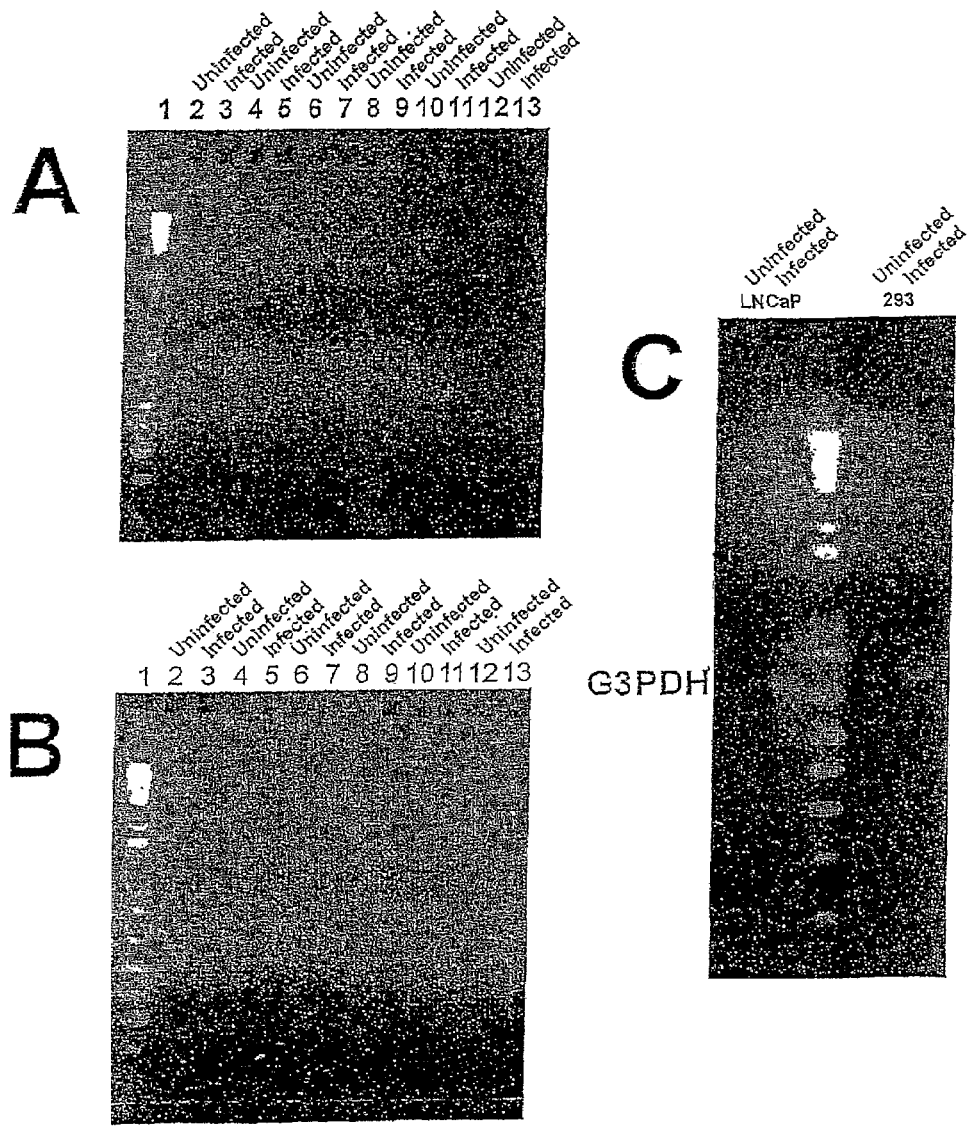
FIG. 2 illustrates the lack of expression of baculoviral encoded genes in mammalian cells.

A further modification of the pBACsurf vector was carried out, in order to facilitate a single recombination step for both of the humanising sequences (ie human promoter and cell surface attachment), whereby a second multiple cloning site (MCS2) was inserted into the recombination area, which contains unique (ie single cut for the plasmid) RE sites. This is shown below:

The alternative method of deriving the multiple recombinants is to co-transfect the promoter vector pBACMAM2 with the singly modified pBACsurf with the Bacvector 1000 triple cut DNA into sf21 insect cells, and to screen for double recombinant viruses by polymerase chain reaction. This is the method of choice when large (>3 kb) promoter fragments are inserted, as the capacity of the pBACsurf (MCS2) vector is limited. Viral DNA from the recombinant plaques therefore is characterised by a wild-type PCR product and a larger product from the insertion recombinant. The sense of the insertion is verified by direct DNA sequencing of the purified PCR product.

Promoter fragments are inserted into the pBACMAM vector to replace the hybrid CAG promoter (CMV enhancer (within Genbank acc.#: AF477200)), Chicken beta actin promoter (Genbank acc.#: E02199) and rabbit beta globin terminator (Genbank acc.#:AX451706). To facilitate this a general insertion construct was prepared in pT7 blue vector, such that the promoter is inserted upstream of either indicator genes (for activity in human cells such as the enhanced green fluorescent protein (EGFP) (Genbank acc.#: U57609) or a hybrid consisting of the EGFP fused to the common bacterial indicator chloramphenicol acetyl transferase or CAT gene (Genbank acc.#: D14641). This construct is then excised from the pT7 blue carrier and inserted via SphI/SwaI and HindIII/BcII sites into the pBACMAM vector. The use of the multiple cloning site in the pBACMAM vector (thus retaining the BgIII, StuI, Sae8387, NotI, KpnI, SmaI, Bsu36 and MacI sites) and inserting the promoter construct upstream of the Rabbit beta globin terminator (Genbank acc.#: AX451706) is also possible.

Gene maps are created in Gene Construction Kit v2 (Textco Inc, USA)

EXAMPLE 1

The baculovirus used to infect one insect and two human cell lines was a recombinant AcMNPV engineered to carry the EGFP reporter gene under the control of the strong mammalian CAG promoter. The human cells were inspected 48 Hrs post infection, using fluorescent microscopy, to visualise the EGFP expression. Significantly, visual inspection suggests the infection efficiency in vitro for the LNCaP prostate cancer cells was equivalent to that of the 293 cells (25% by flow cytometry analysis, data not shown)—no appreciable EGFP expression can be seen from the CAG promoter in insect Sf-9 cells (data not shown). Total RNA was extracted from all cells and RT-PCR carried out using the six sets of primers designed against baculoviral mRNA, plus a G3PDH primer set as a positive control for the human cells.

In the Sf9 cells, expression of four out of the six genes examined was detected via RT-PCR in infected cells and but not in uninfected cells (FIG. 1) indicating baculoviral specific expression. The exceptions to this were the ubiquitin gene and the egt gene. Ubiquitin expression was detected in both infected and uninfected insect cells using the primers designed against baculovirus ubiquitin (FIG. 1), although the levels in uninfected cells were much lower. This can be explained in that ubiquitin is a highly conserved molecule and there may be enough homology between insect and baculoviral ubiquitin to produce an RT-PCR product of the same size. It is also possible that the baculoviral ubiquitin may actually have derived from its insect cell host during evolution. The other exception was the egt gene which was not expressed in either infected or uninfected cells (FIG. 1). Egt is expressed very early in the baculoviral life cycle to prevent larval moulting and Sf9 cells are derived from pupal ovarian tissue. Therefore, it can be hypothesised that there are factors in the larval form of the host which are not found in the pupal stage and are necessary for egt expression.

EXAMPLE 2

For expression analysis in human cells, the 293 human embryonic kidney cell line was chosen due to its reported ease of infection with baculovirus (Condreay J P, Proc. Natl. Acad. Sci. USA 1999; 96: 127-132; Boyce F M, Bucher N L R. Proc. Natl. Acad. Sci. USA 1996; 93:2348-2352) and the wide range of gene it can be induced to express. Additionally, the LNCaP prostate cancer cell line (derived from lymph node metastases) was chosen as a model for prostate cancer gene therapy—especially as these cells are difficult to transduce by liposome based techniques. The results for the RT-PCR for both of these cells lines show that none of the six baculoviral genes examined are expressed in either uninfected or infected cells in either cell line (FIG. 2), despite the high levels of expression of the CAG controlled EGFP. Messenger RNA for the housekeeping gene, G3PDH, was also found in uninfected and infected cells in both of the cells lines using significantly fewer PCR cycles (25 cycles compared to 35 when screening for the baculoviral mRNA). These results indicate that a representative portion of the endogenous genes found in baculovirus, most of which are highly expressed in the normal eukaryotic baculovirus host environment and can interact with essential human cell processes, are not expressed when the virus is used to infect human cells. In contrast protein can be effectively synthesised from a reporter gene under the control of a mammalian promoter. This lack of baculoviral gene expression in human cells further underlines the safety of the baculovirus as a vector for gene therapy, particularly for transient suicide gene protocols, since neither baculoviral gene expression or genome integration will be a likely complication.

TABLE 1

| Promoter sequence | DNA Accession number |
|---|---|
| Prostate androgen regulated transcript 1 | BC026274 or NM005551 |
| Prostate transglutaminase, | BC007003 |
| Prostase | XM031805 |
| Prostate-derived Ets factor | AF071538 |
| Prostatic acid phosphatase | X53605 |
| Pr LeuZip | |
| PAGE-4 | AF275258 |
| DD3 | |
| NKX3.1 | AF247704 |
| probasin | AX259949 |
| prostate-specific antigen | AJ459782 |
| prostate-specific membrane antigen | XM165392 |
| prostate stem cell antigen | XM030742 |
| prostate carcinoma tumor antigen-1 | NM006499 |
| AIPC | AF338650 |
| Trp-p8 | AC005538 |
| E2F4 | AF527540 |
| Daxx | AF015956 |
| TRPM-2 | NM001831 |
| PART-1 | nm016590 |
| TMPRSS2 | |
| Bomesin | |
| Steap | Nm 012449 |
| TARP | Af151103 |
| PcGEM1 | Af223389 |

TABLE 2

| Tumor suppressor Polypeptide | DNA accession number |
|---|---|
| p53 | AF136270 |
| Retinoblastoma | |
| APC polypeptide | NM000038 |
| DPC-4 polypeptide | U73825 |
| BRCA-1 polypeptide | |
| BRCA-2 polypeptide | |
| WT-1 polypeptide | XM_034418 |
| MMAC-1 polypeptide | XM083839 |
| Familial polyposis coli polypeptide | NM000038 |

TABLE 3

| Tumor Rejection Antigen Precursor Family | DNA Accession number |
|---|---|
| MAGE | XM066465 |
| BAGE | NM001187 |
| GAGE | NM_003785 |
| DAGE | Q99958 |

TABLE 4

| Cell-CycleArrest Polypeptide | DNA accession number |
|---|---|
| p21 | NM078467 |
| p16 | NM058196 |
| p15 | BC002010 |
| p18 | BC027026 |
| p19 | NM079421 |
| PTEN | AF143312 |

TABLE 5

| Cytokine | DNA Accession number |
|---|---|
| growth hormone | |
| leptin | |
| erythropoietin | |
| prolactin | |
| IL-2 | XM_035511 |
| IL-3 | U81493 |
| IL-4 | AF395008 |
| IL-5 | AF353265 |
| IL-6 | AF039224 |
| IL-7 | NM000880 |
| IL-9 | AF361105 |
| IL-10 | BC022315 |
| IL-11 | BC012506 |
| the p35 subunit of IL-12 | AF101062 |
| IL-13 | AF377331 |
| IL-15 | AF031167 |
| G-CSF | E09569 |
| GM-CSF | M13207 |
| CNTF | E09734 |
| CT-1 | XM096076 |
| LIF | XM009915 |
| oncostatin M | NM020530 |
| IFNα | J00207 |

TABLE 6

| Apoptosis inducing polypeptide | DNA Accession number |
|---|---|
| P53 | AF136270 |
| adenovirus E3.11.6K | |
| adenovirus E4 | |
| adenovirus f4 | |
| caspase | |
| Fas ligand | E11157 |
| C-Cam 1 | XM113980 |
| ODC | NM052998 |
| OAZ | XM037830 |
| spermidine/spermine N1-acetyltransferase | BC002503 |
| ZNF145 | NM006006 |
| PTEN phosphatase | AF143312 |
| androgen receptor | NM_000044 |
| Bcl2 family members. | |

TABLE 7

| Prodrug Activating polypeptide | DNA Accession number |
|---|---|
| cytosine deaminase | AL627278 |
| thymidine kinase | AB078742 |
| nitroreductase RdxA | AY063488 |
| Cytochrome P450 CYP1A2 | NM_000761 |
| CYP2E1 | AB052259 |
| CYP3A4 | AF209389 |

TABLE 1

Baculoviral genes chosen for expression analysis

| Baculoviral Gene | Gene Function | Stage of Life Cycle Expressed | Human Homologue | Primer Name | Size of PCR Product (bp) |
|---|---|---|---|---|---|
| Proliferating cell nuclear antigen | Stimulates DNA replication and late gene expression | Early | Yes | pcna | 308 |
| DNA polymerase | DNA replication | Early | Yes | DNA-pol | 247 |
| Ubiquitin | Blocks ubiquitin dependent proteolysis | Late | Yes | ubi | 142 |
| gp37 (p34.8) | Spindle body protein | Late/Very Late | No | gp37 | 347 |
| p10 | Viral lysis (?) | Very Late | No | p10 | 202 |
| Ecdysteroid UDP-glucosyltransferase | Blocks larval moulting | Early | No | egt | 281 |

TABLE 2

Cell lines used to investigate native baculovirus gene expression.

| Cell Line | Description |
|---|---|
| Sf-9 | Insect cell line, derived from pupal ovarian tissue of the fall army worm, Spodoptera frugiperda |
| 293 | Human cell line derived from human embryonic kidney and transformed to immortality by adenovirus 5 |
| LNCaP | Androgen-dependent, non-metastatic, non-tumourigenic human prostate cancer cell line derived from lymph node metastasis |

The invention claimed is:

1. A baculovirus wherein the baculovirus genome has been modified to comprise a first polynucleotide which encodes a prodrug activating polypeptide and a second polynucleotide that encodes a baculovirus capsid polypeptide fused to a gonadotropin releasing hormone (GnRH) peptide consisting of the amino acid sequence SEQ ID NO: 2 that binds the baculovirus to the cell surface of a prostate cancer cell.

2. A baculovirus according to claim 1 wherein the expression of said first polynucleotide is controlled by a cancer specific promoter.

3. A baculovirus according to claim 2 wherein said cancer specific promoter is a prostate cancer cell specific promoter.

4. A baculovirus according to claim 1 wherein said prodrug-activating polypeptide is selected from the group consisting of cytosine deaminase, theymidine kinase, nitroreductase RdxA, Cytochrome P450 CYP1A2, Cytochrome P450 CyP2E1 and Cytochrome P450 CYP3A4.

5. A baculovirus according to claim 1 wherein said baculovirus capsid polypeptide is gp64.

6. A pharmaceutical composition comprising the baculovirus according to claim 1 and a pharmaceutically acceptable excipient.

* * * * *